United States Patent [19]

Miyazawa et al.

[11] Patent Number: 5,225,112

[45] Date of Patent: Jul. 6, 1993

[54] SHAMPOO COMPOSITION

[75] Inventors: Kiyoshi Miyazawa; Uhei Tamura; Isao Murotani; Kenichi Tomita, all of Yokohama, Japan

[73] Assignee: Shiseido Company, Ltd., Tokyo, Japan

[21] Appl. No.: 925,288

[22] Filed: Aug. 6, 1992

Related U.S. Application Data

[63] Continuation of Ser. No. 577,560, Sep. 5, 1990, abandoned.

Foreign Application Priority Data

Sep. 5, 1989 [JP] Japan ................................ 1-230907

[51] Int. Cl.$^5$ ............................ C11D 1/28; C11D 1/48; C11D 1/72; C11D 1/88
[52] U.S. Cl. ...................................... 252/545; 252/546; 252/547; 252/548; 252/554; 252/174.19; 252/174.23; 252/DIG. 13; 424/70
[58] Field of Search ............... 252/547, 548, 545, 552, 252/174.23, DIG. 13, 554, 546, 174.19; 424/70

[56] References Cited

U.S. PATENT DOCUMENTS

| | | | |
|---|---|---|---|
| 3,496,110 | 2/1970 | Shumway | 252/142 |
| 3,549,542 | 12/1970 | Holderby | 252/137 |
| 3,996,146 | 12/1976 | Tarasov et al. | 252/142 |
| 4,233,192 | 11/1980 | Lindemann et al. | 252/545 |
| 4,371,517 | 2/1983 | Vanlerberghe et al. | 424/70 |
| 4,847,071 | 7/1989 | Bissett et al. | 424/59 |
| 4,919,846 | 4/1990 | Nakama et al. | 252/542 |
| 4,954,332 | 9/1990 | Bissett et al. | 424/59 |

FOREIGN PATENT DOCUMENTS

| | | |
|---|---|---|
| 127580 | 12/1984 | European Pat. Off. |
| 57-195800 | 12/1982 | Japan |
| 58-138799 | 8/1983 | Japan |

*Primary Examiner*—Paul Lieberman
*Assistant Examiner*—Erin M. Higgins
*Attorney, Agent, or Firm*—Wegner, Cantor, Mueller & Player

[57] ABSTRACT

A shampoo composition containing components (I) to (V) shown below:

(I) at least one alkyloylalkyltaurine salt type anionic surfactant of the formula (A):

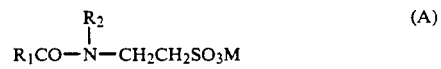

$$R_1CO-\underset{\underset{R_2}{|}}{N}-CH_2CH_2SO_3M \quad (A)$$

wherein $R_1$ represents an alkyl group, an alkenyl group or a hydroxyalkyl group with an average carbon number of 7 to 19, $R_2$ is a lower alkyl group with an average carbon number of 1 to 3, and M an alkali metal or an organic amine;

(II) at least one betaine type amphoteric surfactant;
(III) at least one nonionic surfactant with an HLB of 10 to 16;
(IV) at least one surfactant selected from alkylolamide type nonionic surfactants represented by the formula (B):

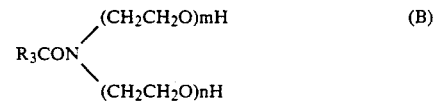

$$R_3CON\begin{cases}(CH_2CH_2O)_mH\\(CH_2CH_2O)_nH\end{cases} \quad (B)$$

wherein $R_3$ represents an alkyl group or an alkenyl group with an average carbon atom of 7 to 19, m and n are integers, and $m+n$ is 1 to 5, and semipolar surfactants;

(V) at least one cationic high molecular weight compound.

1 Claim, No Drawings

SHAMPOO COMPOSITION

This application is a continuation of U.S. application Ser. No. 07/577,560 filed Sept. 5, 1990, now abandoned.

BACKGROUND OF THE INVENTION

1. Field of the Invention

The present invention relates to a shampoo composition, and more specifically, relates to an improvement of the useability or applicability thereof.

2. Description of the Related Art

Damage to the hair caused by chemical treatments such as permanent waving, hair dying, and hair bleaching has long been a problem, and particularly, due to an increased number of these chemical treatments for the hair, an increase in the number of times that the hair is washed, contamination of the hair by air pollution, changes in the social environment such as a drying of hair due to air conditioning, etc., the hair is now far more susceptible to damage. Accordingly, the functions demanded from a shampoo are not merely foaming and washability, but also hair conditioning effects (not causing damage to the hair or repairing damaged hair; a good useability such as easy passing of the fingers therethrough when washing or rinsing the hair, no hair squeak, an easy unification of the hair after drying, pliability, and easy combing, etc.) are now required.

To provide a shampoo with a conditioning effect, frequently used in the art are oily components such as lanolin derivatives, protein derivatives, and higher alcohols, humectants such as glycerine, polyethylene glycol, and propylene glycol, amphoteric or nonionic water-soluble high molecular weight compounds, and natural plant extracts, etc.

These components, however, are poorly adsorbed onto the hair, and are mostly washed away during the rinsing operation after the shampooing, and therefore, do not provide a satisfactory conditioning effect for damaged hair, particularly hair damaged by permanent waving, hair dying and hair bleaching.

On the other hand, as the surfactant formulated in the art as the detergent in shampoos used by experts such as barbers or beauty salons and those for general commercial products, primarily alkylsulfate salts, polyoxyethylene alkylsulfate salts, alkylbenzenesulfonic acid salts, and α-olefin-sulfonic acid salts are frequently used.

Shampoos containing these surfactants, although having a good washing power, are known to more or less irritate the skin, whereby experts subject to frequent changes of shampoos used, such as barbers or beauty salon staff, are susceptible to skin disorders such as hand roughness, etc.

Accordingly, the present inventors previously called attention to the intimate correlation between a protein denaturation power and useability improvement, and developed a detergent composition using a surfactant with a low protein denaturation power (Japanese Unexamined Patent Publication (Kokai) No. 57-195800), or a detergent composition formulated with a specific cationic high molecular weight compound and having an even lower protein denaturation power (Japanese Unexamined Patent Publication (Kokai) No. 58-138799).

Current hair fashions and other developments require that people wash their hair at least 3 to 4 times a week, or even every day, and accordingly, if the hair is washed with a shampoo formulated with a strong surfactant which irritates the skin, the problem of a roughness of the scalp arises, which leads to the generation of dandruff and an itchy scalp.

Accordingly, under the present situation there is an urgent demand for a shampoo which has a conditioning effect suitable for use by barbers and beauty salons, without anxiety, and for general commercial products, and at the same time, having a very low skin irritation effect.

In view of the above, the above-mentioned respective inventions created by the present inventors do not have a required useability, and thus there is a need for the formulation of a shampoo composition having a far better useability.

SUMMARY OF THE INVENTION

Accordingly, the objects of the present invention are to eliminate the above-mentioned disadvantages of the prior art and to provide a shampoo composition having an excellent conditioning effect and a good useability, and at the same time, a markedly lower skin irritation effect.

Other objects and advantages of the present invention will be apparent from the following description.

In accordance with the present invention, there is provided a shampoo composition comprising components (I) to (V) shown below:

(I) at least one alkyloylalkyltaurine salt type anionic surfactant of the formula (A):

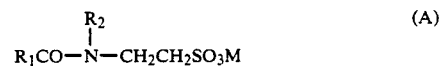

wherein $R_1$ represents an alkyl group, an alkenyl group, or a hydroxyalkyl group with an average carbon number of 7 to 19, $R_2$ is a lower alkyl group with an average carbon number of 1 to 3, and M an alkali metal or an organic amine;

(II) at least one betaine type amphoteric surfactant;

(III) at least one nonionic surfactant with an HLB of 10 to 16;

(IV) at least one surfactant selected from alkylolamide type nonionic surfactants represented by the formula (B):

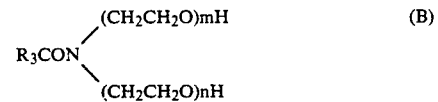

wherein $R_3$ represents an alkyl group or an alkenyl group with an average carbon atom of 7 to 19, m and n are integers, and m+n is 1 to 5, and semipolar surfactants;

(V) at least one cationic high molecular weight compound.

DESCRIPTION OF THE PREFERRED EMBODIMENTS

According to the present invention, by using a specific nonionic surfactant in combination with a surfactant with a low protein denaturation ratio and a cationic high molecular weight compound, the absorption of the cationic high molecular weight compound onto the hair can be increased, to thereby accomplish the present invention.

The shampoo composition according to the present invention may further contain an organic acid.

The components of the shampoo composition according to the present invention will be explained in detail.

Alkyloylalkyltaurine Salt Type Anionic Surfactant

In the present invention, the alkyloylalkyltaurine salt type anionic surfactant represented by the formula (A) includes, for example, as the alkyloyl group, $R_1CO—$, lauryoyl, myristoyl, palmitoyl, stearoyl, oleoyl, cocoloyl groups from coconut oil fatty acid (alkyloyl groups with carbon numbers of $R_1$ being distributed between 7 and 19); as the alkyl group $R_2$, methyl, ethyl, and propyl groups; and as the ion M, lithium, potassium, sodium, triethanolamine, diethanolamine, and monoethanolamine.

Betaine Type Amphoteric Surfactant

The betaine type amphoteric surfactant to be used in the present invention is exemplified by an amidebetaine type surfactant of the formula (E):

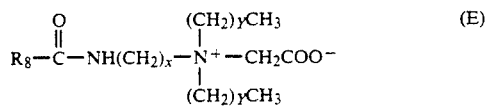

[Typical commercial products are, for example, Rebon (Sanyo Kasei), Anon BDF (Nippon Yushi)];

an amidosulfobetaine type amphoteric surfactant of the formula (F):

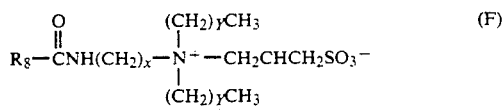

[Typical commercial products are, for example, Ronsaine-CS (Ronsa), Miratine CBS (Milanol), etc.,];

a betaine type amphoteric surfactant of the formula (G):

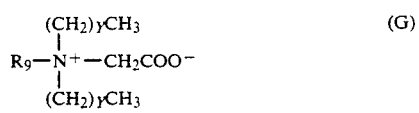

[Typical commercial products are, for example, Anon BL (Nippon Yushi), Dehyton AB-30 (Henkel)];

a sulfobetaine type amphoteric surfactant of the formula (H):

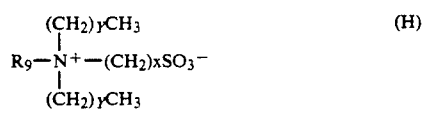

[Typical commercial products are, for example, Ronsaine CS (Ronsa)]; or an imidazolinium type amphoteric surfactant of the formula (I):

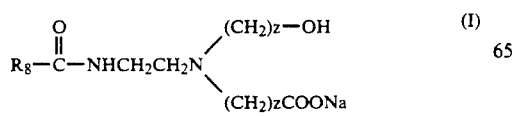

[Typical commercial products are, for example, Obazoline 662-N (Toho Kagaku), Anon GLM (Nippon Yushi), etc.,].

In the above formulae (E) to (I), $R_8$ is an alkyl group or an alkenyl group with an average carbon number of 9 to 17, and $R_9$ is an alkyl group or an alkenyl group with an average carbon number of 10 to 18, x is an integer of 2 to 4, y is an integer of 0 to 3, and z is an integer of 1 or 2.

Nonionic Surfactant

Nonionic surfactants with an HLB of from 10 to 16 are exemplified by the polyoxyethylene alkyl ether type, the polyoxyethylene alkyl-phenylester type, the polyoxyethylene polyoxypropylene alkylester type, the polyoxyethylene polyhydric alcohol fatty acid ester type, the polyglycerine fatty acid ester type, and the polyoxyethylenated castor oil type. Particularly preferable nonionic surfactants in the present invention are the polyoxyethylene alkyl ether type.

HLB is an index indicating the Hydrophilic-Lipophilic Balance, and in the present invention, the values calculated by using the formula according to Oda.-Teramura et al., are employed.

$$HLB = \frac{\Sigma \text{ inorganic value}}{\Sigma \text{ organic value}} \times 10$$

Alkylolamide Type Nonionic Surfactant

The alkylolamide type nonionic surfactant represented by the formula (B) includes, for example, as the alkyloyl group $R_3CO—$, lauroyl, myristoyl, palmitoyl, stearoyl, oleoyl, and cocoloyl from coconut oil fatty acid (alkyloyl groups with carbon numbers of $R_3$ being distributed between 7 and 19).

Semi-Polar Surfactant

The semi-polar surfactant, which is the tertiary amine oxide type semi-polar surfactant, includes the following.

Amine oxide represented by the formula (J):

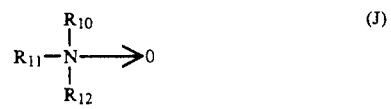

wherein $R_{10}$, $R_{11}$ and $R_{12}$ independently represent a straight or branched alkyl group or alkenyl group having 1 to 24 carbon atoms, and at least one of $R_{10}$, $R_{11}$, and $R_{12}$ represents a straight or branched alkyl group or alkenyl group having 8 or more carbon atoms.

Specific examples of the amine oxide represented by the formula (J) include dimethyllaurylamine oxide, dimethylmyristylamine oxide, dimethylcetylamine oxide, dimethylstearylamine oxide, dimethyloleylamine oxide, dimethylbehenylamine oxide, methyldilaurylamine oxide, and the like.

Also, there can be employed dihydroxyethylalkylamine oxide represented by the formula (K):

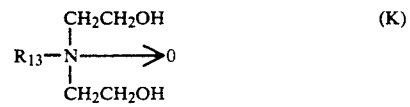

wherein $R_{13}$ represents a straight or branched alkyl or alkenyl group having 8 to 24 carbon atoms, and dimethylalkylpolyoxyethyleneamine oxide represented by the formula (L):

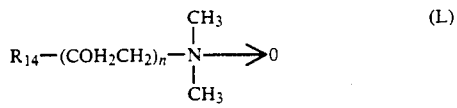

$$R_{14}-(COH_2CH_2)_n-\overset{CH_3}{\underset{CH_3}{N}}\rightarrow O \qquad (L)$$

wherein $R_{14}$ represents a straight or branched alkyl group or alkenyl group having 8 to 24 carbon atoms, and n represents an integer of 1 to 5.

Cationic High Molecular Weight Compound

The cationic high molecular weight composition includes a poly(dimethyldiallylammonium halide) type cationic high molecular weight compound represented by the formula (C):

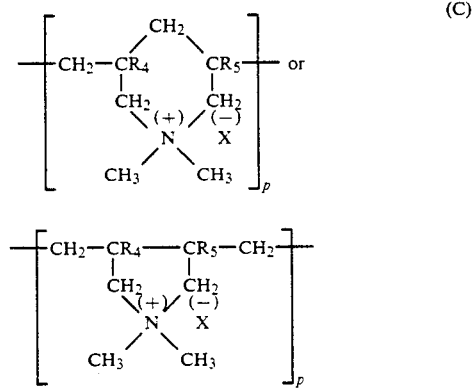

wherein $R_4$ and $R_5$ represent a hydrogen atom H or methyl group —$CH_3$, X is a halogen, and P is an integer of from 150 to 6,200; or a copolymer type cationic high molecular weight compound of dimethyldiallylammonium halide and acrylamide represented by the formula (D):

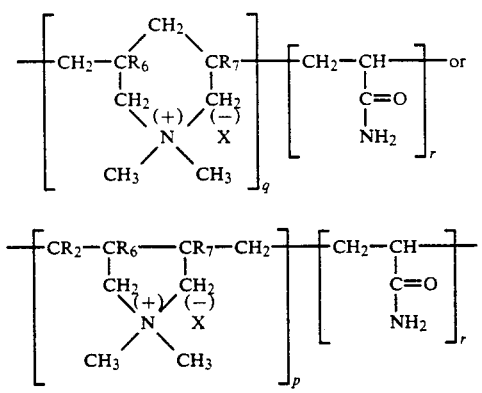

wherein $R_6$ and $R_7$ represent a hydrogen atom H or methyl group —$CH_3$, X is a halogen, and q+r is an integer of from 150 to 9,000.

The X in the poly(dimethylammonium halide) type cationic high molecular weight compound represented by the formula (C) is a halogen such as chloro and bromo, and the chloro thereamong is available from Merck & Co., Inc., U.S.A. under the trade name of Merquat 100. Merquat 100 is an aqueous solution of about 40% of a pure component, and is a pale yellow viscous liquid.

The X in the dimethyldiallylammonium halide and acrylamide copolymer type cationic high molecular weight compound represented by the formula (D) is a halogen such as chloro and bromo. The copolymer is expressed conveniently by the formula (D), but need not be a block type copolymer. The sequence of the monomers may be as desired, but one wherein X is chloro is available from Merck & Co. U.S.A. under the Trademark of Merquat 550. Merquat 550 is an aqueous solution of about 8% pure components, and is a colorless viscous liquid.

The condensed product of polyethylene glycol, epichlorohydrin, propylene amine and tallowylamine or cocoylamine as the cationic high molecular weight compound is available from Henkel international Co. under the Trademark of Polyquart H. Polyquart H is an aqueous solution of about 50% pure component, and is a pale yellow viscous liquid.

The quaternary nitrogen containing cellulose ether as the cationic high molecular weight compound is available from Union Carbide Corp. U.S.A. under the Trademarks of Polymer JR-400, Polymer JR-125, and Polymer JR-30M, which are white (pale yellow) powders.

Organic Acid

Examples of the organic acid to be used in the present invention are citric acid, lactic acid, and tartaric acid.

By thus formulating an organic acid, an improvement of the stability of the nonionic surfactant can be effected, and a separation or decomposition thereof can be effectively prevented.

The amount formulated is preferably 0.001 to 2% by weight, more preferably 0.01 to 1.5% by weight, of the total amount of the shampoo composition.

Since the organic acid is used for the improvement of the stability of the nonionic surfactant, the formulation ratio thereof is intimately correlated, and preferably the organic acid/nonionic surfactant ratio is 0.0001 to 3.

At a weight ratio of 0.0001 or less, the stability is not sufficiently improved, and at a weight ratio of 3 or more, the pH of the shampoo composition is greatly lowered, to thereby affect the stability of the other surfactants.

Formulation Amount and Formulation Ratio

The preferable formulation amounts of the above-mentioned active ingredients are:

3 to 30 parts by weight of the taurine salt type anionic surfactant represented by (I);

3 to 30 parts by weight of the betaine type amphoteric surfactant represented by (II);

the formulation ratio (by weight) of (I):(II) being about 3:1 to about 1:2;

0.1 to 5 parts by weight of the nonionic surfactant with an HLB of 10 to 16 represented by (III);

0.1 to 5 parts by weight of the alkylolamide type nonionic surfactant and the semi-polar surfactant represented by (IV); and 0.001 to 3 parts by weight of the cationic high molecular weight compound represented by (V).

Preferably, (I)+(II)+(III)+(IV) are used in an amount of about 10 to 50 parts by weight of the total amount.

The present inventors found that, when the alkyloylalkyltaurine salt type anionic surfactant represented by the above (I) and the betaine type amphoteric surfactant represented by (II) are mixed at an appropriate formulation ratio, phenomena such as an elevation of the craft point, elevation of the viscosity, elevation of the pH, and lowering of the critical micelle concentration are observed, and thus estimated that a complex of the anionic surfactant and the amphoteric had been formed.

It has been found that, in this mixture, the surface active abilities such as foaming and washability are improved and are superior to those obtained by each individual component, and at the same time, the protein denaturation is markedly lowered compared with that of each individual component.

The adequate formation ratio (by weight) of (I):(II) is within the range of from about 3:1 to about 1:2, preferably as close to 1:1 as possible. When the mixing ratio is outside this range, or when the balance of the system is destroyed by an addition of a large amount of other anionic surfactants, a sufficient lowering of the protein denaturation ratio cannot be obtained.

The alkylolamide type nonionic surfactant and the semi-polar surfactant represented by (IV) to be used in the present invention have been formulated in the art in anionic surfactant type shampoos, to provide improved effects of an increased foaming, increased viscosity, and low temperature stability, and in the present invention, it has been found that a further lowering of the protein denaturation ratio occurs when (IV) is formulated in the above-mentioned mixture of (I) and (II). A preferable ratio (by weight) of (I) (II):(IV) is within the range of from about 15:1 to about 1:1 in terms of weight ratio. If (I)+(II) is more than this ratio, the lowering of protein denaturation ratio of (IV) is unsatisfactory, and if the amount of (IV) is too high, the washing power and foaming power required from the shampoo will be reduced. Preferably, (I)+(II)+(IV) comprise about 10 to about 50 parts by weight of the total liquid shampoo.

The nonionic surfactant with an HLB of 10 to 16 represented by (III) and used in the present invention, can be used in combination with the cationic high molecular weight compound represented by (V), which is formulated particularly for an enhancement of the useability of the shampoo compositions by an increase of the adsorption of the cationic high molecular compound onto the hair, and to provide a greater useability than that obtained when formulated into only other bases. Preferably, the formulation ratio is within the range of about 10:1 to about 1:2 of (III):(V), more preferably close to 2:1. If the mixing ratio is outside this range, the useability of the cationic high molecular weight compound is the same as that when it is used alone, and thus an increase of the amount adsorbed onto the hair cannot be obtained.

Other Components

If desired, the shampoo composition of the present invention can include components generally formulated in shampoos, for example, oily components such as higher alcohols, lanolin derivatives, protein derivatives or fatty acid esters of polyethylene glycols; humectant components such as propylene glycol, glycerine, and polyethylene glycols; water-soluble high molecular weight substances such as polyethylene oxide polypropylene oxide block polymers; and sequestering agents, preservatives, sterilizing agents, pH controllers, UV-ray absorbers, antioxidants, dyes and perfumes, etc.

As described above, the present inventors have created a low skin irritation effect conditioning shampoo having a low protein denaturation ratio, a good storability as a shampoo, a good useability when washing hair, a good finish after hair washing and drying, while maintaining the low skin irritation effect, by formulating a specific nonionic surfactant into a specific shampoo composition.

EXAMPLES

The present invention will now be further illustrated by, but is by no means limited to, the following Examples.

First, the test methods and evaluation methods employed in the respective Examples are described.

Foaming Test Method

An amount of 400 ml of a sample solution having a 1% by weight concentration was prepared with artificial $CaCO_3$ 70 ppm hard water, and the foaming amount was measured by using a cylinder equipped with a stirrer under a temperature of 40° C.

| | |
|---|---|
| ○ ... Good foaming: | foam amount of 2000 ml or more |
| Δ ... Normal foaming: | foam amount of 1500 ml to 2000 ml |
| x ... Poor foaming: | foam amount of less than 1500 ml |

Washability Test Method

A sample solution having a 1% by weight concentration was prepared with artificial CaO/MgO=3/1 5°DH hard water, and an artificially soil contaminated cloth of wool serge was washed.

The cloth was washed by a Targotometer (JIS K-3371), under a temperature of 40° C., and the washing effect determined from the reflectances before and after washing.

$$\text{Washing effect (\%)} = \frac{R_W - R_S}{R_0 = R_S} \times 100$$

$R_0$: reflectance of original cloth (wool serge)
$R_S$: reflectance of contaminated cloth after washing
$R_W$: reflectance of contaminated cloth after washing
○ ... Good washability: washing efficiency of 80% or more
Δ ... Normal washability: washing efficiency of 60% or more and less than 80%
x ... Poor washability: washing efficiency of less than 60%

Protein Denaturation Measurement Method

Utilizing an aqueous system high performance liquid chromatography, the denaturation of ovalbumin when a sample was added to a sample having a concentration of in an ovalbumin pH 7 buffer solution, was measured by obtaining the absorption peak at 220 nm.

$$\% \text{ Protein denaturation} = \frac{H_0 - H_S}{H_0} \times 100$$

$H_0$: height of 220 nm absorption peak of ovalbumin buffer solution
$R_S$: height of 220 nm absorption peak when sample is added to ovalbumin buffer solution
⊚ ... % Protein denaturation: less than 30%
○ ... % Protein denaturation: 30% or more less than 60%
Δ ... % Protein denaturation: 60% or more, less than 80%
x ... % Protein denaturation: 80% or more

Hand Roughness Test Method

Each sample was tested by a panel of 10 members, 5 men and 5 women, who dipped either the left or right hand in an aqueous solution of a sample having a concentration of 5%, at a temperature of 35° C., and the other hand in water at the same temperature, for 10 minutes twice a day, continuously for 2 days, and the difference in the skin roughening states of the left and right hands was judged by the naked eye.

- ⊚ ... very little hand roughening, hand roughening recognized on the sample side in 0 to 1 member of panel
- ○ ... slight hand roughening, hand roughening recognized on the sample side in 2 to 4 members of panel
- Δ ... stronger hand roughening, hand roughening recognized on the sample side in 5 to 7 members of panel
- x ... remarkable strong hand roughening, hand roughening recognized on the sample side in 8 to 10 members of panel

Method of Measuring Amount of Dandruff Generated

Panel members, who usually used a general commercially available lauryl ether sulfate type shampoo (containing no medicament for dandruff and itchy scalp), were asked to wash their hair, at the same frequency as usual and by the same washing method as usual, 5 times while using a sample, and the amounts of dandruff before and after the use of the sample were compared. The amount of dandruff on the third day after washing with a general commercially available shampoo, and the amount of dandruff on the third day after the final day when hair was washed 5 times with the sample, were measured. Dandruff was collected by aspiration from the head, by an aspiration device equipped with a filter cloth, and the nitrogen amount was determined by the Kjeldahl method, to eliminate errors due to the presence of other foreign matter, and the average protein mass was determined by multiplying the measured value by 6.25, and was defined as the amount of dandruff (mg/head). Three panel members were used for each sample, and a comparison was made on the basis of average values.

- ⊚ ... 30% or more reduction of amount of dandruff after using sample
- ○ ... 10% or more but less than 30% reduction of amount of dandruff after using sample
- Δ ... 0% or more but less than 10% reduction of amount of dandruff after using sample
- x ... amount of dandruff increased after using sample

Stability Test Method

A shampoo composition was stored under the conditions of 0° C., 25° C., and 50° C. for one month, and the appearance thereof observed with the naked eye.

- ⊚ ... very good stability, transparent dissolution or slightly turbid state under the respective temperature conditions, but no separation, agglomeration or precipitation observed
- ○ ... good stability, slight turbidity recognized under 50° C. storage, but no problems arise during use
- Δ ... not good stability, slight turbidity formed under respective temperature conditions
- x ... poor stability, separation, agglomeration, and precipitation observed.

Test Method of Useability During Hair Washing (Half Head Method)

The panel members parted their hair into left and right halves; one of which was washed with a general commercially available shampoo of lauryl ether sulfate type as Control, and the other was washed with a sample, at the same time, and the passing of the fingers therethrough during washing and rinsing, and presence of hair squeak were evaluated organoleptically, for a comparison.

- ⊚ ... much better useability than Control
- ○ ... slightly better useability than Control
- Δ ... same useability as Control
- x ... inferior useability to Control

Test Method of Finish of Hair after Washing and Drying

After the panel members had washed their hair according to the same method as described above (half head method), the hair was dried and the finish state, such as the ease of unification of the left and right side hair, pliability, unkemptness, stiffness, and good or bad comb passing ability, was evaluated organoleptically, for a comparison.

- ⊚ ... much better finish state than Control
- ○ ... slightly better finish state than Control
- Δ ... same finish state as Control
- x ... inferior finish state to Control Test Example 1: Effect of Addition of Nonionic Surfactant A shampoo composition having the following formulation was prepared. A conventional preparation method was used.

| Formulation: | | % by weight |
|---|---|---|
| (I) | Lauroylmethyltaurine-Na | 10 |
| (II) | Lauryldimethylaminoacetic acid betaine | 8 |
| (III) | Polyoxyethylene (average 12 moles) lauryl ether | x |
| (IV) | Coconut fatty acid diethanolamide | 4 |
| (V) | Poly(dimethyldiallylammonium chloride) | y |
| | Water | balance |

In the above formulation, the formulated amount x of polyoxyethylene lauryl ether (nonionic surfactant), and the formulated amount y of poly(dimethylallylammonium chloride) (cationic high molecular weight compound) were successively varied, and the various characteristics thereof were examined.

The results are shown in the following Tables 1 (A) to (I).

TABLE 1 (A)

| | y = 0 | | | | | | | |
|---|---|---|---|---|---|---|---|---|
| | Amount of x formulated | | | | | | | |
| | 0.005 | 0.01 | 0.1 | 0.5 | 1.0 | 2.0 | 4.0 | 5.0 |
| Foamability | ○ | ○ | ○ | ○ | ○ | ○ | ○ | Δ |
| Washability | ○ | ○ | ○ | ○ | ○ | ○ | ○ | ○ |
| % Protein denaturation | ○ | ○ | ○ | ○ | ⊚ | ⊚ | ⊚ | ⊚ |
| Amount of dandruff generated | ○ | ○ | ○ | ○ | ○ | ⊚ | ○ | ○ |
| Stability | Δ | Δ | Δ | Δ | Δ | Δ | Δ | Δ |
| Useability during hair washing | Δ | Δ | Δ | Δ | Δ | Δ | Δ | Δ |
| Finish of hair after washing and drying | Δ | Δ | Δ | Δ | Δ | Δ | Δ | Δ |

TABLE 1 (B)

y = 0.005

| Amount of x formulated | 0.005 | 0.01 | 0.1 | 0.5 | 1.0 | 2.0 | 4.0 | 5.0 |
|---|---|---|---|---|---|---|---|---|
| Foamability | ○ | ○ | ○ | ○ | ○ | ○ | ○ | △ |
| Washability | ○ | ○ | ○ | ○ | ○ | ○ | ○ | ○ |
| % Protein denaturation | ○ | ○ | ○ | ○ | ⊙ | ⊙ | ⊙ | ○ |
| Amount of dandruff generated | ○ | ○ | ○ | ○ | ⊙ | ⊙ | ○ | ○ |
| Stability | △ | △ | △ | △ | △ | △ | △ | △ |
| Useability during hair washing | △ | △ | △ | △ | △ | △ | △ | |
| Finish of hair after washing and drying | △ | △ | △ | △ | △ | △ | △ | |

TABLE 1 (C)

y = 0.01

| Amount of x formulated | 0.005 | 0.01 | 0.1 | 0.5 | 1.0 | 2.0 | 4.0 | 5.0 |
|---|---|---|---|---|---|---|---|---|
| Foamability | ○ | ○ | ○ | ○ | ○ | ○ | ○ | ○ |
| Washability | ○ | ○ | ○ | ○ | ○ | ○ | ○ | ○ |
| % Protein denaturation | ○ | ○ | ○ | ○ | ⊙ | ⊙ | ⊙ | ○ |
| Amount of dandruff generated | ○ | ○ | ○ | ○ | ⊙ | ⊙ | ○ | ○ |
| Stability | △ | △ | △ | △ | △ | △ | △ | △ |
| Useability during hair washing | ○ | ○ | ○ | ○ | ○ | ○ | ○ | ○ |
| Finish of hair after washing and drying | ○ | ○ | ○ | ○ | ○ | ○ | ○ | ○ |

TABLE 1 (D)

y = 0.05

| Amount of x formulated | 0.005 | 0.01 | 0.1 | 0.5 | 1.0 | 2.0 | 4.0 | 5.0 |
|---|---|---|---|---|---|---|---|---|
| Foamability | ○ | ○ | ○ | ○ | ○ | ○ | ○ | ○ |
| Washability | ○ | ○ | ○ | ○ | ○ | ○ | ○ | ○ |
| % Protein denaturation | ○ | ○ | ○ | ○ | ⊙ | ⊙ | ⊙ | ⊙ |
| Amount of dandruff generated | ○ | ○ | ○ | ○ | ⊙ | ⊙ | ⊙ | ⊙ |
| Stability | △ | △ | △ | △ | △ | △ | △ | △ |
| Useability during hair washing | ○ | ○ | ⊙ | ○ | ○ | ○ | ○ | ○ |
| Finish of hair after washing and drying | ○ | ○ | ⊙ | ○ | ○ | ○ | ○ | ○ |

TABLE 1 (E)

y = 0.1

| Amount of x formulated | 0.005 | 0.01 | 0.1 | 0.5 | 1.0 | 2.0 | 4.0 | 5.0 |
|---|---|---|---|---|---|---|---|---|
| Foamability | ○ | ○ | ○ | ○ | ○ | ○ | ○ | ○ |
| Washability | ○ | ○ | ○ | ○ | ○ | ○ | ○ | ○ |
| % Protein denaturation | ○ | ○ | ○ | ○ | ⊙ | ⊙ | ⊙ | ⊙ |
| Amount of dandruff generated | ○ | ○ | ○ | ○ | ⊙ | ⊙ | ⊙ | ○ |
| Stability | △ | △ | △ | △ | △ | △ | △ | △ |
| Useability during hair washing | ○ | ○ | ○ | ⊙ | ○ | ○ | ○ | ○ |
| Finish of hair after washing and drying | ○ | ○ | ○ | ⊙ | ○ | ○ | ○ | ○ |

TABLE 1 (F)

y = 0.5

| Amount of x formulated | 0.005 | 0.01 | 0.1 | 0.5 | 1.0 | 2.0 | 4.0 | 5.0 |
|---|---|---|---|---|---|---|---|---|
| Foamability | ○ | ○ | ○ | ○ | ○ | ○ | ○ | ○ |
| Washability | ○ | ○ | ○ | ○ | ○ | ○ | ○ | ○ |
| % Protein denaturation | ○ | ○ | ○ | ⊙ | ⊙ | ⊙ | ⊙ | ⊙ |
| Amount of dandruff generated | ○ | ○ | ○ | ○ | ⊙ | ⊙ | ⊙ | ○ |
| Stability | △ | △ | △ | △ | △ | △ | △ | |
| Useability during hair washing | ○ | ○ | ○ | ⊙ | ⊙ | ⊙ | ○ | ○ |
| Finish of hair after washing and drying | ○ | ○ | ○ | ⊙ | ⊙ | ⊙ | ○ | ○ |

TABLE 1 (G)

y = 1.0

| Amount of x formulated | 0.005 | 0.01 | 0.1 | 0.5 | 1.0 | 2.0 | 4.0 | 5.0 |
|---|---|---|---|---|---|---|---|---|
| Foamability | ○ | ○ | ○ | ○ | ○ | ○ | ○ | ○ |
| Washability | ○ | ○ | ○ | ○ | ○ | ○ | ○ | ○ |
| % Protein denaturation | ○ | ○ | ○ | ⊙ | ⊙ | ⊙ | ⊙ | ⊙ |
| Amount of dandruff generated | ○ | ○ | ○ | ○ | ⊙ | ⊙ | ⊙ | ⊙ |
| Stability | △ | △ | △ | △ | △ | △ | △ | △ |
| Useability during hair washing | ○ | ○ | ○ | ○ | ○ | ⊙ | ⊙ | ○ |
| Finish of hair after washing and drying | ○ | ○ | ○ | ○ | ○ | ⊙ | ⊙ | ○ |

TABLE 1 (H)

y = 3.0

| Amount of x formulated | 0.005 | 0.01 | 0.1 | 0.5 | 1.0 | 2.0 | 4.0 | 5.0 |
|---|---|---|---|---|---|---|---|---|
| Foamability | ○ | ○ | ○ | ○ | ○ | ○ | ○ | △ |
| Washability | ○ | ○ | ○ | ○ | ○ | ○ | ○ | ○ |
| % Protein denaturation | ○ | ○ | ○ | ○ | ○ | ⊙ | ⊙ | ⊙ |
| Amount of dandruff generated | ○ | ○ | ○ | ○ | ○ | ⊙ | ⊙ | ⊙ |
| Stability | △ | △ | △ | △ | △ | △ | △ | △ |
| Useability during hair washing | ○ | ○ | ○ | ○ | ○ | ○ | ⊙ | ⊙ |
| Finish of hair after washing and drying | ○ | ○ | ○ | ○ | ○ | ○ | ⊙ | ⊙ |

TABLE 1 (I)

y = 4.0

| Amount of x formulated | 0.005 | 0.01 | 0.1 | 0.5 | 1.0 | 2.0 | 4.0 | 5.0 |
|---|---|---|---|---|---|---|---|---|
| Foamability | ○ | ○ | ○ | ○ | ○ | ○ | ○ | △ |
| Washability | ○ | ○ | ○ | ○ | ○ | ○ | ○ | ○ |
| % Protein denaturation | ○ | ○ | ○ | ○ | ○ | ○ | ○ | ○ |
| Amount of dandruff generated | ○ | ○ | ○ | ○ | ○ | ○ | ○ | ○ |
| Stability | △ | △ | △ | △ | △ | △ | △ | △ |
| Useability during hair washing | ○ | ○ | ○ | ○ | ○ | ○ | ⊙ | ⊙ |
| Finish of hair after washing and drying | ○ | ○ | ○ | ○ | ○ | ○ | ○ | ⊙ |

As apparent from the Tables, when the cationic high molecular compound is not contained (A), or when contained in a very small amount (B), no great change occurs even if a nonionic surfactant is added.

Nevertheless, when a cationic high molecular compound is added in an amount of 0.01% or more, and further, a nonionic surfactant is added, great change in the useability occurs, depending on its amount added.

Namely, as apparent from the above Tables 1 (C) to (H), when a cationic high molecular weight compound is added in an amount of 0.01 to 3% by weight or more, an improvement of the useability can be recognized, and when a nonionic surfactant is added in an amount of 10-to ½-fold, relative to the above cationic high molecular weight compound, an improvement of the useability, due to the synergistic effect with the cationic high molecular weight compound, can be observed. Particularly, by an addition of a nonionic surfactant in an amount about 2-fold or more of the cationic high molecular weight compound, remarkable synergistic effects can be observed with respect to the useability during hair washing, and in the hair finish after hair drying.

From the results described above, a very specific synergistic effect of a cationic high molecular weight compound and a nonionic surfactant was confirmed, and it is clear that this synergistic effect is greatest at a ratio of a nonionic surfactant to a cationic high molecular weight compound of 10:1 to 1:2, particularly about 2:1.

Test Example 2: Effect of Addition of Organic Salt

A shampoo composition having the following formulation was prepared. A conventional preparation method was used.

| Formulation: | % by weight |
|---|---|
| (I) Lauroylmethyltaurine-Na | 10 |
| (II) Lauryldimethylaminoacetic acid betaine | 8 |
| (III) Polyoxyethylene (average 12 moles) lauryl ether | x |
| (IV) Coconut fatty acid diethanolamide | 4 |
| (V) Poly(dimethyldiallylammonium chloride) | 1.0 |
| (VI) Citric acid | z |
| Water | balance |

In the above formulation, the amount x formulated of polyoxyethylene lauryl ether (nonionic surfactant), and the amount z formulated of citric acid (organic acid) were successively varied, and the various characteristics thereof were examined.

The results are shown in Tables 2 (A) to (G).

TABLE 2 (A)

$x = 0$

| | Amount of z formulated | | | | | | | | |
|---|---|---|---|---|---|---|---|---|---|
| | 0.0005 | 0.001 | 0.01 | 0.02 | 0.1 | 1.0 | 1.5 | 2.0 | 3.0 |
| Foamability | ○ | ○ | ○ | ○ | ○ | ○ | ○ | Δ | Δ |
| Washability | ○ | ○ | ○ | ○ | ○ | ○ | ○ | ○ | Δ |
| % Protein denaturation | ○ | ○ | ○ | ○ | ○ | ○ | ○ | ○ | ○ |
| Amount of dandruff | ○ | ○ | ○ | ○ | ○ | ○ | ○ | ○ | ○ |
| Stability | Δ | Δ | Δ | Δ | Δ | Δ | × | × | × |
| Useability during hair washing | ○ | ○ | ○ | ○ | ○ | ○ | ○ | ○ | ○ |
| Finish of hair after washing and drying | ○ | ○ | ○ | ○ | ○ | ○ | ○ | ○ | ○ |

TABLE 2 (B)

$x = 0.01$

| | Amount of z formulated | | | | | | | | |
|---|---|---|---|---|---|---|---|---|---|
| | 0.0005 | 0.001 | 0.01 | 0.02 | 0.1 | 1.0 | 1.5 | 2.0 | 3.0 |
| Foamability | ○ | ○ | ○ | ○ | ○ | ○ | ○ | Δ | Δ |
| Washability | ○ | ○ | ○ | ○ | ○ | ○ | ○ | ○ | ○ |
| % Protein denaturation | ○ | ○ | ○ | ○ | ○ | ○ | ○ | ○ | ○ |
| Amount of dandruff | ○ | ○ | ○ | ○ | ○ | ○ | ○ | ○ | ○ |
| Stability | Δ | ○ | ○ | ○ | ○ | Δ | × | × | × |
| Useability during hair washing | ○ | ○ | ○ | ○ | ○ | ○ | ○ | ○ | ○ |
| Finish of hair after washing and drying | ○ | ○ | ○ | ○ | ○ | ○ | ○ | ○ | ○ |

TABLE 2 (C)

$x = 0.1$

| | Amount of z formulated | | | | | | | | |
|---|---|---|---|---|---|---|---|---|---|
| | 0.0005 | 0.001 | 0.01 | 0.02 | 0.1 | 1.0 | 1.5 | 2.0 | 3.0 |
| Foamability | ○ | ○ | ○ | ○ | ○ | ○ | ○ | Δ | Δ |
| Washability | ○ | ○ | ○ | ○ | ○ | ○ | ○ | ○ | ○ |
| % Protein denaturation | ○ | ○ | ○ | ○ | ○ | ○ | ○ | ○ | ○ |
| Amount of dandruff | ○ | ○ | ○ | ○ | ○ | ○ | ○ | ○ | ○ |
| Stability | Δ | ○ | ○ | ⊙ | ⊙ | Δ | × | × | × |
| Useability during hair washing | ○ | ○ | ○ | ○ | ○ | ○ | ○ | ○ | ○ |
| Finish of hair after washing and drying | ○ | ○ | ○ | ○ | ○ | ○ | ○ | ○ | ○ |

TABLE 2 (D)

$x = 0.5$

| | Amount of z formulated | | | | | | | | |
|---|---|---|---|---|---|---|---|---|---|
| | 0.0005 | 0.001 | 0.01 | 0.02 | 0.1 | 1.0 | 1.5 | 2.0 | 3.0 |
| Foamability | ○ | ○ | ○ | ○ | ○ | ○ | ○ | ○ | Δ |
| Washability | ○ | ○ | ○ | ○ | ○ | ○ | ○ | ○ | ○ |
| % Protein denaturation | ⊙ | ⊙ | ⊙ | ⊙ | ⊙ | ⊙ | ⊙ | ⊙ | ⊙ |
| Amount of dandruff | ○ | ○ | ○ | ○ | ○ | ○ | ○ | ○ | ○ |
| Stability | Δ | ○ | ○ | ⊙ | ⊙ | ○ | ○ | Δ | × |
| Useability during hair washing | ○ | ○ | ○ | ○ | ○ | ○ | ○ | ○ | ○ |
| Finish of hair after washing and drying | ○ | ○ | ○ | ○ | ○ | ○ | ○ | ○ | ○ |

TABLE 2 (E)

$x = 1.0$

| | Amount of z formulated | | | | | | | | |
|---|---|---|---|---|---|---|---|---|---|
| | 0.005 | 0.001 | 0.01 | 0.02 | 0.1 | 1.0 | 1.5 | 2.0 | 3.0 |
| Foamability | ○ | ○ | ○ | ○ | ○ | ○ | ○ | ○ | Δ |
| Washability | ○ | ○ | ○ | ○ | ○ | ○ | ○ | ○ | ○ |
| % Protein denaturation | ⊙ | ⊙ | ⊙ | ⊙ | ⊙ | ⊙ | ⊙ | ⊙ | ⊙ |
| Amount of dandruff generated | ⊙ | ⊙ | ⊙ | ⊙ | ⊙ | ⊙ | ⊙ | ⊙ | ⊙ |
| Stability | Δ | ○ | ○ | ⊙ | ⊙ | ⊙ | ○ | Δ | × |
| Useability during hair washing | ○ | ○ | ○ | ○ | ○ | ○ | ○ | ○ | ○ |
| Finish of hair after washing and drying | ○ | ○ | ○ | ○ | ○ | ○ | ○ | ○ | ○ |

TABLE 2 (F)

$x = 2.0$

| | Amount of z formulated | | | | | | | | |
|---|---|---|---|---|---|---|---|---|---|
| | 0.005 | 0.001 | 0.01 | 0.02 | 0.1 | 1.0 | 1.5 | 2.0 | 3.0 |
| Foamability | ○ | ○ | ○ | ○ | ○ | ○ | ○ | ○ | Δ |
| Washability | ○ | ○ | ○ | ○ | ○ | ○ | ○ | ○ | ○ |
| % Protein denaturation | ⊙ | ⊙ | ⊙ | ⊙ | ⊙ | ⊙ | ⊙ | ⊙ | ⊙ |
| Amount of dandruff generated | ⊙ | ⊙ | ⊙ | ⊙ | ⊙ | ⊙ | ⊙ | ⊙ | ⊙ |
| Stability | Δ | ○ | ○ | ⊙ | ⊙ | ⊙ | ○ | ○ | × |
| Useability during | ⊙ | ⊙ | ⊙ | ⊙ | ⊙ | ⊙ | ⊙ | ⊙ | ⊙ |

TABLE 2 (F)-continued

| | x = 2.0 | | | | | | | | |
|---|---|---|---|---|---|---|---|---|---|
| | Amount of z formulated | | | | | | | | |
| | 0.005 | 0.001 | 0.01 | 0.02 | 0.1 | 1.0 | 1.5 | 2.0 | 3.0 |
| hair washing | | | | | | | | | |
| Finish of hair after washing and drying | ⊚ | ⊚ | ⊚ | ⊚ | ⊚ | ⊚ | ⊚ | ⊚ | ⊚ |

TABLE 2 (G)

| | x = 5.0 | | | | | | | | |
|---|---|---|---|---|---|---|---|---|---|
| | Amount of z formulated | | | | | | | | |
| | 0.005 | 0.001 | 0.01 | 0.02 | 0.1 | 1.0 | 1.5 | 2.0 | 3.0 |
| Foamability | ○ | ○ | ○ | ○ | ○ | ○ | ○ | ○ | △ |
| Washability | ○ | ○ | ○ | ○ | ○ | ○ | ○ | ○ | ○ |
| % Protein denaturation | ⊚ | ⊚ | ⊚ | ⊚ | ⊚ | ⊚ | ⊚ | ⊚ | ⊚ |
| Amount of dandruff generated | ⊚ | ⊚ | ⊚ | ⊚ | ⊚ | ⊚ | ⊚ | ⊚ | ⊚ |
| Stability | △ | ○ | ○ | ⊚ | ⊚ | ⊚ | ○ | ○ | x |
| Useability during hair washing | ○ | ○ | ○ | ○ | ○ | ○ | ○ | ○ | ○ |
| Finish of hair after washing and drying | ○ | ○ | ○ | ○ | ○ | ○ | ○ | ○ | ○ |

As apparent from the above Tables 2, the addition of an organic acid when a nonionic surfactant is not present (A) will not improve the stability.

Nevertheless, when 0.001 to 2% by weight of an organic acid is added, in the presence of a nonionic surfactant, the stability is improved. Particularly, a good improvement of the stability was observed at 0.01 to 1.5% by weight of organic acid/0.0001 to 3 of nonionic surfactant.

This suggests that the presence of the organic acid is closely related to the stability of nonionic surfactant, and that the nonionic surfactant will be separated and decomposed if the organic acid is not present.

At a level of 2% by weight or more of organic acid, the pH of the shampoo composition is lowered, and thus the stability of the other surfactants is adversely influenced.

Specific examples of the present invention are described as follows.

EXAMPLES 1-12

Shampoo compositions comprising the formulation compositions shown in the following Table 3 were prepared, and the foaming, washability, % protein denaturation, hand roughness, amount of dandruff generated, stability, useability during hair washing, and finish of hair after hair washing and drying, were examined. The results are shown in Table 3 (Examples of the present invention and Comparative Examples).

(* - 1) Merquat 100 (Merck), aqueous solution of about 40% pure component
(* - 2) Merquat 550 (Merck), aqueous solution of about 8% pure component
(* - 3) Polymer JR-400 (Union Carbide), white to pale yellow powder

TABLE 3 (A)

| | | 1 | 2 | 3 | 4 | 5 | 6 |
|---|---|---|---|---|---|---|---|
| I | Lauroylmethyltaurine-Na | 15 | 10 | 20 | 7 | 10 | 10 |
| II | Lauryldimethylaminoacetic acid betaine (formula G Y = 1) | 4 | 8 | — | — | 10 | 5 |
| II | Lauroylimidazolinium betaine (formula Z = 1) | — | — | 16 | 18 | — | 5 |
| III | Polyoxyethylene (average 12 moles) lauryl ether | 1 | 3 | 0.5 | 1 | — | — |
| III | Polyoxyethylene (average 15 moles) stearyl ether | — | — | — | — | 2 | — |
| III | Polyoxyethylene (average 40 moles) hardened castor oil | — | — | — | — | — | 0.5 |
| IV | Coconut fatty acid diethanolamide | ⊚ | 4 | 2.5 | 3 | — | 2 |
| IV | Lauryldimethylamine oxide | — | — | — | — | 4 | 2 |
| V | Poly(dimethyldiallyl ammonium chloride) *-1 | 0.5 | 0.5 | 1.5 | 0.8 | — | — |
| V | Copolymer *-2 | — | — | — | — | — | 1.0 |
| V | Quaternary nitrogen containing cellulose ether *-3 | — | — | — | — | 0.3 | — |
| | Citric acid | — | 0.1 | — | 0.1 | — | 0.1 |
| | Water | | | Balance | | | |
| Foamability | | ○ | ○ | ○ | ○ | ○ | ○ |
| Washability | | ○ | ○ | ○ | ○ | ○ | ○ |
| % Protein denaturation | | ○ | ⊚ | ○ | ⊚ | ⊚ | ⊚ |
| Hand roughness | | ○ | ⊚ | ○ | ⊚ | ⊚ | ○ |
| Amount of dandruff generated | | ○ | ⊚ | ○ | ⊚ | ⊚ | ⊚ |
| Stability | | ○ | ⊚ | ○ | ⊚ | △ | ⊚ |
| Useability during hair washing | | ⊚ | ⊚ | ⊚ | ⊚ | ⊚ | ⊚ |
| Finish of hair after washing and drying | | ⊚ | ⊚ | ⊚ | ⊚ | ⊚ | ⊚ |

TABLE 3 (B)

| | | 7 | 8 | 9 | 10 | 11 | 12 |
|---|---|---|---|---|---|---|---|
| I | Lauroylmethyltaurine-Na | 10 | ⊚ | 20 | 20 | 7 | 7 |
| II | Lauryldimethylaminoacetic acid betaine (formula G Y = 1) | 10 | 5 | 10 | 10 | 5 | 5 |
| II | Lauroylimidazolinium betaine (formula Z = 1) | 10 | — | 5 | 5 | — | — |
| III | Polyoxyethylene (average 12 moles) lauryl ether | 0.5 | 0.5 | 2 | 2 | 0.5 | 5 |
| III | Polyoxyethylene (average 15 moles) stearyl ether | 0.5 | — | — | — | — | — |
| III | Polyoxyethylene (average 40 moles) hardened castor oil | — | — | 1 | 1 | — | — |
| IV | Coconut fatty acid diethanolamide | 0.2 | 0.2 | 2.5 | 1.5 | 3 | 3 |
| IV | Lauryldimethylamine oxide | 1.5 | 0.5 | 2.5 | 1 | 2 | 2 |
| V | Poly(dimethyldiallyl ammonium chloride) *-1 | 1.2 | — | 1.0 | 1.0 | 1.0 | 0.5 |
| V | Copolymer *-2 | — | — | — | — | — | — |
| V | Quaternary nitrogen containing cellulose ether *-3 | — | 0.5 | — | — | 0.3 | — |
| | Citric acid | — | 0.1 | — | 0.1 | — | 0.1 |
| | Water | | | Balance | | | |
| Foamability | | ○ | ○ | ○ | ○ | ○ | ○ |
| Washability | | ○ | ○ | ○ | ○ | ○ | ○ |
| % Protein denaturation | | ⊚ | ⊚ | ⊚ | ⊚ | ⊚ | ⊚ |
| Hand roughness | | ○ | ⊚ | ⊚ | ⊚ | ○ | ⊚ |
| Amount of dandruff generated | | ○ | ⊚ | ⊚ | ○ | ○ | ⊚ |
| Stability | | ○ | ⊚ | △ | ⊚ | ○ | ⊚ |
| Useability during hair washing | | ⊚ | ○ | ⊚ | ⊚ | ○ | ○ |
| Finish of hair after washing and drying | | ⊚ | ○ | ⊚ | ⊚ | ○ | ○ |

The shampoo compositions according to the present invention exhibited a very good foaming, washability, protein denaturation, hand roughness, amount of dandruff generated, stability, useability during hair washing, and finish of the hair after hair washing and drying.

EXAMPLE 13

A shampoo comprising the following formulation composition was prepared.

| | % by weight |
|---|---|
| Cocoloylmethyltaurine-Na | 8 |
| Laurylamidepropyl betaine | ○ |
| Polyoxyethylene (ED average 15 moles) | 2 |

-continued

|  | % by weight |
|---|---|
| lauryl ether (HLB 14.1) |  |
| Lauric acid diethanolamide | 5 |
| Glycerine | 2 |
| Poly(dimethyldiallylammonium chloride) | 0.8 |
| Citric acid | 0.1 |
| Perfume | 0.3 |
| Water | balance |
|  | 100 |

This shampoo was subjected to the same evaluation tests as in Test Example 1, to determine the foamability o, washability o, % protein denaturation ⊚, hand roughness ⊚, amount of dandruff generated ⊚, stability ⊚, useability during hair washing ⊚, and finish after hair washing and drying ⊚.

EXAMPLE 14

A shampoo comprising the following formulation composition was prepared.

|  | % by weight |
|---|---|
| Ethylene glycol fatty acid ester | 1.5 |
| Lauroylmetyltaurine-Na | 10 |
| Cocoyldimethylacetic acid betaine | 8 |
| Polyoxyethylene (average 17 moles) cetyl ether (HLB 13.6) | 2 |
| Coconut fatty acid diethanolamide | 4 |
| Lauryldimethylamine oxide | 1 |
| Propylene glycol | 2 |
| Vinyl pyrrolidone/dimethylaminoethyl methacrylate copolymer cationized product | 0.5 |
| Perfume | 0.3 |
| Water | balance |
|  | 100 |

The same evaluation tests of this cream type shampoo were made as in Example 1, and the foamability o, washability o, % protein denaturation ⊚, hand roughness ⊚, amount of dandruff generated ⊚, stability o (opaque cream type), useability during hair washing ⊚, and finish after hair washing and drying ⊚ results were obtained.

EXAMPLE 15

A shampoo comprising the following formulation composition was prepared.

|  | % by weight |
|---|---|
| Diethylene glycol fatty acid ester | 2 |
| Lauroylpropyltaurine-Na | 10 |
| Lauryldipropylaminoacetic acid betaine | 8 |
| Polyoxyethylene (average 40 moles) hardened castor oil (HLB 12.2) | 2 |
| Oleyldimethylamine oxide | 3 |
| Poly(dimethyldiallylammonium chloride) | 0.5 |
| Hydroxyethylcellulose cationized product | 0.2 |
| Perfume | 0.3 |
| Water | balance |
|  | 100 |

The same evaluation tests of this cream type shampoo were made as in Example 1, and the foamability o, washability o, % protein denaturation ⊚, hand roughness ⊚, amount of dandruff generated ⊚, stability o (opaque cream type), useability during hair washing ⊚, and finish after hair washing and drying ⊚ results were obtained.

As described above, according to the shampoo composition of the present invention, since a nonionic surfactant is contained together with a cationic high molecular weight compound, the adsorption of the above-mentioned cationic high molecular weight compound onto the hair is improved, whereby the useability of the shampoo composition is also improved.

Also, by containing an organic acid together with the above-mentioned nonionic surfactant, the stability of the nonionic surfactant can be greatly improved.

We claim:

1. A shampoo composition comprising components (I) to (VI) shown below:

(I) 3 to 30 parts by weight of at least one alkyloylalkyltaurine salt anionic surfactant of the formula (A):

$$R_1CO-\underset{\underset{R_2}{|}}{N}-CH_2CH_2SO_3M \qquad (A)$$

wherein $R_1$ represents an alkyl group, an alkenyl group or a hydroxyalkyl group with an average carbon number of 7 to 19, $R_2$ is a lower alkyl group with an average carbon number of 1 to 3, and M is an alkali metal or an organic amine;

(II) 3 to 30 parts by weight of at least one betaine amphoteric surfactant selected from the group consisting of betaine amphoteric surfactants, sulfobetaine amphoteric surfactants, amide-betaine amphoteric surfactants, amidosulfobetaine amphoteric surfactants, and imidazoliniumbetaine amphoteric surfactants;

(III) 0.1 to 5 parts by weight of at least one nonionic surfactant with an HLB of 10 to 16 selected from the group consisting of polyoxyethylene alkyl ether, polyoxyethylene alkylphenyester, polyoxyethylene polyoxypropylene alkylester, polyoxyethylene polyhydric alcohol fatty acid ester, polyglycerine fatty acid ester, and polyoxyethylenated castor oil nonionic surfactants;

(IV) 0.1 to 5 parts by weight of at least one surfactant selected from the group consisting of alkylolamide nonionic surfactants represented by the formula (B):

$$R_3CON\begin{matrix}(CH_2CH_2O)mH \\ \diagdown \\ (CH_2CH_2O)nH\end{matrix} \qquad (B)$$

wherein $R_3$ represents an alkyl group or an alkenyl group with an average carbon number of 7 to 19, m and n are integers, and m+n is 1 to 5, and tertiary amineoxide semi-polar surfactants;

(V) 0.001 to 3 parts by weight of at least one cationic high molecular weight compound selected from the group consisting of (i) poly(dimethyldiallylammonium halide) cationic high molecular weight compounds represented by the formula (C):

(C)
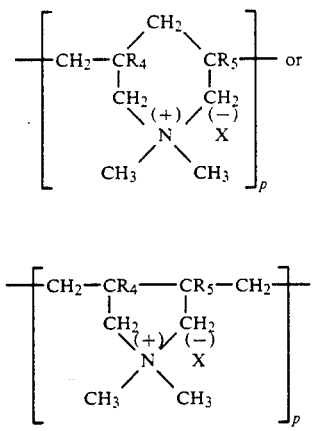

wherein $R_4$ and $R_5$ represent a hydrogen atom or methyl group, X is a halogen, and P is an integer of from 150 to 6,200; (ii) copolymer cationic high molecular weight compound of dimethyldiallylammonium halide and acrylamides represented by the formulae (D):

(D)
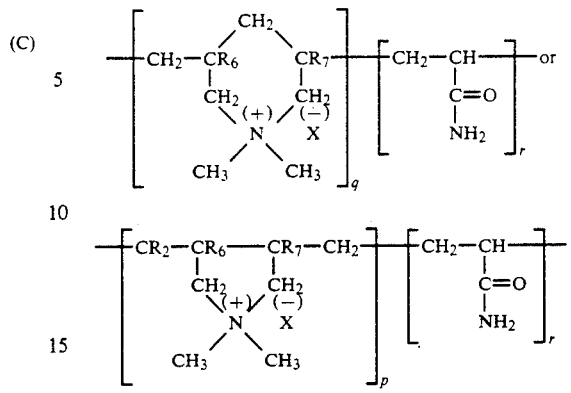

wherein $R_6$ and $R_7$ represent a hydrogen atom or methyl group, X is a halogen, and $q+r$ is an integer of from 150 to 9,000; (iii) condensed products of a polyethylene glycol, epichlorohydrin, propyleneamine and tallowylamine obtained from tallow fatty acid, and condensed products of a polyethylene glycol, epichlorohydrin, propyleneamine and cocoylamine obtained from coconut oil fatty acid; and (iv) quaternary nitrogen containing cellulose ethers, the formulation ratio of the compounds (III)/(V) being 10/1 to 1/2; and (VI) 0.001 to 2.0 parts by weight of an organic acid.

* * * * *